US010768132B2

(12) United States Patent
Rajagopalan et al.

(10) Patent No.: US 10,768,132 B2
(45) Date of Patent: Sep. 8, 2020

(54) DEVICE FOR MEASURING THE CONDUCTIVITY OF A LIQUID IN ORDER TO DETERMINE VERY LOW LEVELS OF TOTAL ORGANIC CARBON (TOC) IN PURE AND ULTRA-PURE WATER

(71) Applicant: Merck Patent GmbH, Darmstadt (DE)

(72) Inventors: Pascal Rajagopalan, Palaiseau (FR); Yves Gaignet, Montigny le Bretonneux (FR); Celine Le Ninivin Glipa, Verneuil sur Seine (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/889,590

(22) PCT Filed: Apr. 14, 2014

(86) PCT No.: PCT/EP2014/000993
§ 371 (c)(1),
(2) Date: Nov. 6, 2015

(87) PCT Pub. No.: WO2014/183824
PCT Pub. Date: Nov. 20, 2014

(65) Prior Publication Data
US 2016/0084784 A1    Mar. 24, 2016

(30) Foreign Application Priority Data
May 15, 2013  (EP) .................... 13290107

(51) Int. Cl.
*G01N 27/06*   (2006.01)
*G01N 33/18*   (2006.01)
*G01N 27/08*   (2006.01)

(52) U.S. Cl.
CPC ......... *G01N 27/06* (2013.01); *G01N 33/1846* (2013.01); *G01N 27/08* (2013.01)

(58) Field of Classification Search
CPC ........ G01N 22/31; G01N 27/06; G01N 27/07; G01N 27/08; G01N 33/1846; G01N 33/1826
See application file for complete search history.

(56) References Cited

U.S. PATENT DOCUMENTS 4,357,576 A * 11/1982 Hickam ................. G01N 27/07
                                                        324/449
4,626,413 A   12/1986 Blades et al.
(Continued)

FOREIGN PATENT DOCUMENTS

CA    2181676 C    2/2004
CN    1449492 A    10/2003
(Continued)

OTHER PUBLICATIONS

Chinese communication, with English translation, dated Aug. 18, 2016 in corresponding Chinese patent application No. 201480027866.X.
(Continued)

*Primary Examiner* — Son T Le
*Assistant Examiner* — Dustin R Dickinson
(74) *Attorney, Agent, or Firm* — Nields, Lemack & Frame, LLC

(57) ABSTRACT

The present patent application relates to a device (1) for measuring the conductivity of a liquid, which comprises a measuring chamber for containing a sampling volume to be irradiated with UV rays formed in a hydraulic body (4) which comprises an inlet channel for feeding the measuring chamber with liquid to be measured and an outlet channel for removing the measured liquid from the measuring chamber, the inlet channel and the outlet channel emerging on either side beyond a surface exposed to the UV rays, such that only the sampling volume contained in the measuring chamber is irradiated. The present patent application is also
(Continued)

Figure 1:
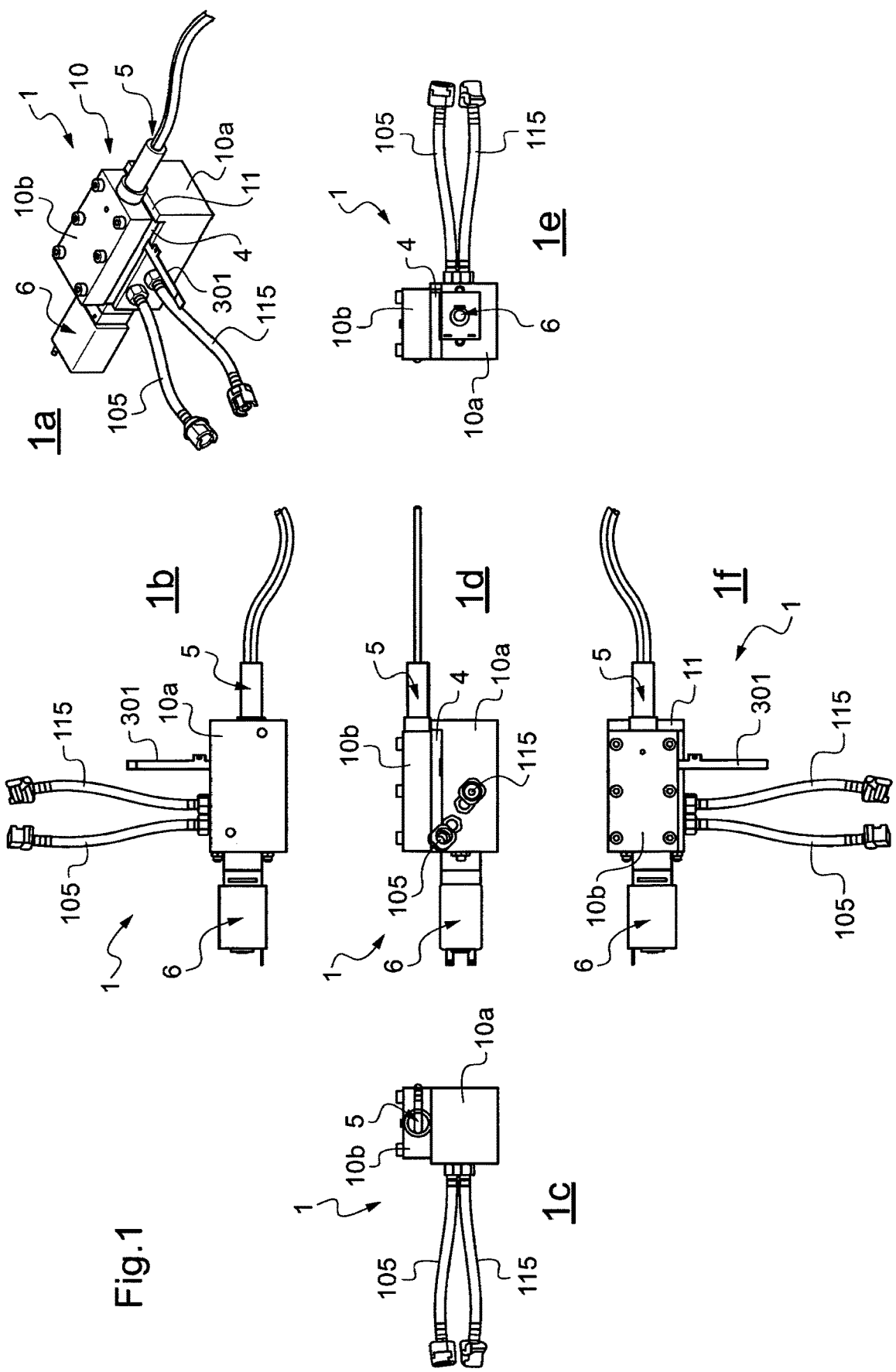

directed towards a use of such a device and to a purification system comprising such a device.

10 Claims, 8 Drawing Sheets

(56) References Cited

U.S. PATENT DOCUMENTS

| | | | |
|---|---|---|---|
| 5,132,094 A * | 7/1992 | Godec | G01N 27/06 422/68.1 |
| 5,275,957 A | 1/1994 | Blades et al. | |
| 5,483,166 A * | 1/1996 | Olsen | G01N 27/07 324/446 |
| 6,444,474 B1 | 9/2002 | Thomas et al. | |
| 7,598,086 B2 * | 10/2009 | Zhao | G01N 27/305 422/78 |
| 7,977,094 B2 * | 7/2011 | Masinaei | A61K 35/32 435/325 |
| 8,557,597 B2 * | 10/2013 | Akechi | G01N 33/1846 422/78 |
| 2002/0125898 A1 * | 9/2002 | Pane | G01N 33/1846 324/693 |
| 2003/0211626 A1 * | 11/2003 | Davenport | G01N 27/021 436/146 |
| 2004/0248306 A1 * | 12/2004 | Hernandez | B01L 3/5027 436/39 |
| 2005/0258839 A1 * | 11/2005 | Gaignet | G01N 27/07 324/696 |
| 2009/0004061 A1 | 1/2009 | Fujiyama et al. | |
| 2010/0070201 A1 * | 3/2010 | Bell | G01N 33/18 702/30 |
| 2010/0291670 A1 * | 11/2010 | Martin | A61L 15/56 435/287.9 |
| 2012/0062243 A1 | 3/2012 | Dimitrakopoulos et al. | |
| 2013/0209991 A1 * | 8/2013 | Wang | A61B 5/1473 435/5 |

FOREIGN PATENT DOCUMENTS

| | | |
|---|---|---|
| CN | 101221141 A | 7/2008 |
| EP | 1927849 A1 | 6/2008 |
| JP | 52-49855 A | 4/1977 |
| JP | 60-159642 A | 8/1985 |
| JP | 63-233370 A | 9/1988 |
| JP | 2008-139312 A | 6/2008 |

OTHER PUBLICATIONS

International Search Report dated Jul. 16, 2014 in corresponding PCT application No. PCT/EP2014/000993.

Chinese communication, with English translation, dated Apr. 21, 2017 in corresponding Chinese patent application No. 201480027866.X.

Japanese communication, with English translation, dated Dec. 22, 2017 in corresponding Japanese patent application No. 2016-513241.

* cited by examiner

Fig.12

| | Thickness (e) (mm) | Length (L) (mm) | Width (l) (mm) | Surface area (s) exposed to UV (mm²) | Surface area (S) of irradiated material (mm²) | Volume (V) of fluid (µl) | S/V ratio (mm²/µl) |
|---|---|---|---|---|---|---|---|
| US6444474 | 0.15 | 20 | 10 | 200 | 409 | 30 | 13.6 |
| | 0.15 | 30 | 6.7 | 201 | 413 | 30 | 13.7 |
| | 0.15 | 14 | 7 | 98 | 202 | 15 | 13.8 |
| | 0.15 | 18.4 | 8 | 147 | 302 | 22 | 13.7 |
| | 0.1 | 18.4 | 8 | 147 | 300 | 15 | 20.4 |
| | 0.1 | 5 | 3 | 15 | 32 | 2 | 21.1 |
| | 0.05 | 18.4 | 8 | 147 | 297 | 7 | 40.4 |
| Examples of implementation of the present invention | 2.7 | 18.4 | 8 | 147 | 437 | 397 | 1.1 |
| | 2 | 18.4 | 8 | 147 | 400 | 294 | 1.4 |
| | 1.5 | 18.4 | 8 | 147 | 374 | 221 | 1.7 |
| | 1 | 18.4 | 8 | 147 | 347 | 147 | 2.4 |
| | 0.5 | 18.4 | 8 | 147 | 321 | 74 | 4.4 |
| | 2.7 | 25 | 10 | 250 | 689 | 675 | 1.0 |
| | 2 | 25 | 10 | 250 | 640 | 500 | 1.3 |
| | 1.5 | 25 | 10 | 250 | 605 | 375 | 1.6 |
| | 1 | 25 | 10 | 250 | 570 | 250 | 2.3 |
| | 0.5 | 25 | 10 | 250 | 535 | 125 | 4.3 |
| | 2.7 | 10 | 4 | 40 | 156 | 108 | 1.4 |
| | 2 | 10 | 4 | 40 | 136 | 80 | 1.7 |
| | 1.5 | 10 | 4 | 40 | 122 | 60 | 2.0 |
| | 1 | 10 | 4 | 40 | 108 | 40 | 2.7 |
| | 0.5 | 10 | 4 | 40 | 94 | 20 | 4.7 |
| | 2.7 | 5 | 3 | 15 | 73 | 41 | 1.8 |
| | 2 | 5 | 3 | 15 | 62 | 30 | 2.1 |
| | 1.5 | 5 | 3 | 15 | 54 | 23 | 2.4 |
| | 1 | 5 | 3 | 15 | 46 | 15 | 3.1 |
| | 0.5 | 5 | 3 | 15 | 38 | 8 | 5.1 |

DEVICE FOR MEASURING THE CONDUCTIVITY OF A LIQUID IN ORDER TO DETERMINE VERY LOW LEVELS OF TOTAL ORGANIC CARBON (TOC) IN PURE AND ULTRA-PURE WATER

The present invention relates, in general, to a device for measuring the conductivity of a pure or even ultra-pure liquid or fluid, especially ultra-pure water, in particular for devices for measuring organic substances or total organic carbon (TOC) in a liquid or fluid sample.

The invention is more particularly directed towards such a device for measurements at very low levels of impurities (typically less than 500 or even 5 ppb (parts per billion) in an ultra-pure fluid or liquid, such as an ultra-pure water, i.e. the conductivity of which is in practice less than 0.055 µS/cm (i.e. less than 0.055 micro-Siemens per centimetre).

The invention is also directed towards a material for making at least part of a measuring cell.

Many modern technological applications require, for their functioning, an ultra-pure water, in particular in the chemical, pharmaceutical, medical and electronic industries.

In theoretically ultra-pure water, the only two ionic species present originate from the dissociation of the water molecules into $H^+$ and $OH^-$.

Thus, at 25°, the theoretical conductivity of a sample of water free of ionic contaminants is equal to 0.055 µS/cm, i.e. a resistivity (inverse of the conductivity) equal to 18.2 MΩ.cm.

This conductivity is measured by applying an electrical potential between two measuring electrodes immersed in the water sample. It is determined from the voltage and the intensity of the current produced inside a conductivity measuring chamber.

It is recalled, in this regard, that conductivity is the measurement of the flow of electrons passing through a substance. It is directly proportional to the ion concentration, to the charge borne by each of these ions (valency) and to their mobility. This mobility depends on the temperature and, consequently, the conductivity measurement also depends on the temperature.

Specifically, one of the major problems in the field of measuring conductivity is that it is greatly affected by temperature variations: the higher the temperature of a sample, the lower its resistivity (due to the mobility of the ions). Thus, to ensure precise measurement, it is necessary to compensate for the temperature in the conductivity measurement. To this end, conductivity measuring cells are generally equipped with sample-temperature sensors.

A temperature sensor, which is in practice in the form of a thermistor, is generally intended to be placed either upstream or downstream of the conductivity measuring cell or, better still, placed under one of the electrodes with, optionally, a thin glass interface between the temperature sensor and a chamber receiving the sample to be measured. Calibration in such a device is thus facilitated by the integration of a thermistor leading to better temperature and conductivity measurement precision.

This conductivity measurement is also affected by the geometry of the chamber receiving the sample.

This is particularly important in the case of ultra-pure water.

In practice, a sample of theoretically ultra-pure water is subjected to photo-oxidation by means of ultraviolet (UV) rays, which makes it possible to measure the amount of organic carbon present in the water from the decrease in resistivity resulting from the ultraviolet oxidation of the organic substances present in the water sample subjected to the measurement.

Now, it is preferable that the surface area (S) of materials exposed to the UV rays be as small as possible to minimise leaching of the materials during the flow of fluid in the chamber (the smaller the amount of pollutants, the better the measurement), but while at the same time conserving the largest possible sampling volume (V) to have a better yield and better efficacy. In other words, it is preferable to have a ratio (S/V) that is as small as possible. In parallel, the smaller the sample volume, the shorter the time required for measuring the conductivity (direct measurement) of ultra-pure water or of any other ultra-pure liquid to be measured.

For example, document EP 1 927 849 is known, which describes a conductivity measuring device comprising a measuring cell composed of a window that is transparent to ultraviolet (UV) rays and provided with a measuring chamber for receiving the liquid sample to be measured, and a substrate comprising electrodes forming a base of the chamber. The substrate thus has a twofold function, namely a measuring function (since it comprises electrodes) and a hydraulic function since it comprises holes for feeding and emptying the measuring chamber. Such a design of the substrate leads to a high cost price and also to weakened mechanical strength (especially when the substrate is initially thin) due to the presence of the holes which have had to be made therein. The presence of the holes also implies minimum dimensions to be respected in terms of length and width for the design of the chamber. The design of the window comprising the chamber, in monobloc manner, is also difficult, complicated and expensive. Moreover, in such a design, the holes for the inlet and outlet of fluid in the chamber are facing the UV rays which naturally penetrate inside. The sampling volume is consequently difficult to determine due to the uncertainty relating to the volumes irradiated by these holes.

Document U.S. Pat. No. 6,444,474 is also known, for example, which describes a conductivity measuring device that allows rapid oxidation of the organic compounds present in the fluid containing up to 100 ppm (the term "rapid" means herein that the reaction lasts from about 2 to 30 seconds according to the said document), and also rinsing of the sensor. According to certain embodiments, the device comprises a cell formed in three independent parts, namely a UV-transparent upper substrate comprising an electrode, a lower substrate comprising another electrode and a separator comprising a cavity, such that the chamber is thus formed by assembling the three elements. The chamber has a small volume (V) (less than 30 µl) and a thickness of less than 150 µm. The device uses two specific electrodes for obtaining photo-catalysis during the UV irradiation and is also composed of materials which are such that they constitute sources of pollution of the fluid (leaching), which increases the conductivity of the fluid and thus makes it impossible to take measurements at very low ppb levels. By virtue of its dimensions, the chamber of the device described has here a ratio between the surface area of the irradiated materials (S) and its volume (V) of the order of 14 mm²/µl. Finally, holes are also formed in the lower substrate to feed and empty the fluid chamber, giving rise, inter alia, to at least some of the abovementioned drawbacks.

Consequently, a subject of the present invention, conceived more specifically for the analysis of TOC below 500 ppb on waters with a conductivity of between 0.055 and 1 µS/cm at 25° C. (i.e. pure or even ultra-pure waters), is, generally, a device for at least partially solving the above-mentioned drawbacks, and also leading to other advantages.

More precisely, a subject of the invention is firstly a device for measuring the conductivity of a liquid, such as pure or ultra-pure water (having, for example, a conductivity of less than 1 µS/cm and less than 500 ppb), comprising a measuring chamber for containing a sampling volume to be irradiated with UV rays, a UV-transparent window being located between the measuring chamber and a source of UV rays, hermetically closing a first side of the measuring chamber, characterised in that the chamber is formed from a hydraulic body, the measuring chamber opening at least on the first side onto a first surface of the hydraulic body, the UV-transparent window covering at least part of the first surface, closing the measuring chamber hermetically on the side of the first surface, and in that the hydraulic body comprises an inlet channel for feeding the measuring chamber with liquid to be measured and an outlet channel for removing the measured liquid from the measuring chamber, the inlet channel and the outlet channel emerging on either side beyond a surface exposed to UV rays, such that only the sampling volume contained in the measuring chamber is irradiated.

Such a device makes it possible to measure very low levels of TOC (typically below 500 ppb and preferably 5 ppb) of oxidisable elements converted into $CO_2$ (carbon dioxide), by irradiation of a source of UV (ultraviolet) rays, with a wavelength typically between 160 nm and 400 nm (nanometres), in a pure water and even in an ultra-pure water (i.e., respectively, 1 µS/cm and 0.055 µS/cm).

Such positioning of the water inlet and outlet ports in the chamber makes it possible to reduce an active surface of the base of the chamber (generally comprising a sensor), and to be able better to determine the sampling volume contained in the chamber since the ports (holes) are now beyond the position facing the UV rays.

To further reduce the surface area of the chamber, the device is also, for example, free of photo-catalysis electrodes.

According to one embodiment, the hydraulic body comprises an inlet to which is connected on the one hand the inlet channel, and an outlet to which is connected on the one hand the outlet channel, the inlet channel and the outlet channel emerging on the other hand in the chamber via a side wall laterally delimiting the measuring chamber.

Thus, since the UV rays are facing the base of the chamber, the rays can no longer penetrate into the depths of the inlet and outlet channels. In addition, the UV rays are generally emitted parallel to the side wall of the chamber, this wall being, for example, of parallelepiped overall shape.

According to one embodiment, the measuring chamber is closed on one side of a second surface of the hydraulic body via a base forming an integral part of the hydraulic body.

According to one embodiment, the measuring chamber is hermetically closed on one side of a second surface of the hydraulic body via a substrate comprising at least two conductivity measuring electrodes, the substrate being applied against at least part of the second surface of the hydraulic body such that the electrodes are facing the measuring chamber.

For example, the inlet and the outlet are formed in the hydraulic body beyond a defined contact surface between the substrate and the second surface.

Such a device makes it possible especially to avoid having to make a hole in the substrate or to machine it, which mechanically embrittles it.

Thus, the substrate, supporting the electrodes forming the sensor which are made here by a printed circuit on the substrate, is independent of the hydraulic circuit, and in particular of the hydraulic body comprising the mechanical elements relating to the flow of fluid; it is thus, for example, unnecessary to pierce the substrate.

Furthermore, the hydraulic body also disassociates the functions associated with the presence of a UV-transparent window, which makes it possible to use a material that is not transmissive from this point of view to make the hydraulic body.

This independence of the hydraulic body for forming the chamber also affords greater latitude of design, as is detailed later in this description.

To improve the flow, especially by minimising potential appearances of bubbles, for example, the inlet channel and the outlet channel each comprise at least one portion emerging in the chamber parallel to the window.

In order also to improve the rinsing of the device, and especially of the measuring chamber, the shape of the chamber and the circulation of the fluid are to be designed so as to avoid residual zones, where the fluid might stagnate or be blocked, leading, for example, to losses of pressure. The circulation of the fluid is very important, not only to prevent bubbles from being trapped during the oxidation reactions, but also to facilitate the rinsing of the cell before oxidation.

In order at least partly to overcome these drawbacks, an inlet and an outlet in the chamber are parallel or even tangential to the sensor (the electrodes), facilitating the removal of bubbles and promoting the rinsing, and preferably, during its use, the cell is positioned vertically, i.e. such that the inlet of fluid into the chamber is positioned at the bottom and the outlet of the fluid from the chamber is positioned at the top.

Failing this, it is preferable for the electrodes to be located under the window to ensure that the electrodes are correctly immersed in the sample to perform the measurements.

According to certain particular arrangements, a portion of the inlet channel and a portion of the outlet channel emerge in the chamber parallel to the window and are each formed in the hydraulic body by a groove hollowed into the part of the first surface covered with the UV-transparent window.

This allows, for example, a simpler preparation of the hydraulic body, especially for the production of pipes, and during its use enables the hydraulic circuit, especially the pipes, to be cleaned more easily.

Furthermore, according to a particular design of the device, any zone promoting pressure losses during rinsing is avoided, and, to do this, for example, at least one from among the inlet channel and the outlet channel has a rounded bend. The existence of an acute angle and/or of a zone with a low flow rate is then avoided. Such a configuration minimises the flow turbulence and affords the most laminar flow possible, especially when the channels comprise a deviation. This may also be promoted, independently or in combination, by rounded or chamfered corners of the side wall of the measuring chamber which has, for example, a rectangular overall shape.

According to one embodiment of the invention, the second surface of the hydraulic body comprises a recess delimited by a contour surrounding the chamber to position the substrate comprising electrodes such that the electrodes are facing the measuring chamber, and the recess being hollowed into the hydraulic body and having a size adjusted to the substrate to house it therein.

According to another embodiment of the invention, the first surface of the hydraulic body comprises a recess delimited by a contour surrounding the measuring chamber, to position the UV-transparent window, and the recess being hollowed into the hydraulic body and having a size adjusted to the window to house it therein.

Furthermore, it is advantageous for the substrate to support the measuring and electrical connection functions, for example by means of an electrical tape, also referred to herein as "FPC" (flexible printed circuit board) brazed thereon. The whole assembly is simplified from a mechanical point of view. To this end, according to one embodiment, the second surface of the hydraulic body comprises a hollow to pass a brazed FPC onto the substrate.

The device also comprises, for example, a case in two parts in which is housed the cell (i.e. the assembly formed of the window, the hydraulic body and the substrate), and means for assembling by holding the two parts together, which are capable of ensuring the leak-tightness of the conductivity measuring cell.

An upper part forms, for example, a support for holding a UV lamp and a lower part forms, for example, a mounting base. The support for the UV lamp, i.e. the upper part of the case, enables, for example, assembly of the set of mechanical components more quickly and more easily, and makes it possible to establish a precise alignment of these elements.

The hydraulic body also makes it possible to protect O-ring seals that are present, for example, around the fluid inlet and outlet of the hydraulic body, and other elements. Specifically, for example in the device described in document EP 1 927 849 mentioned previously, the O-ring seals were directly exposed to UV rays, which brought about rapid or even premature ageing of the irradiated elements.

Furthermore, by means of the present invention, the sample volume is readily reproducible. Moreover, the volumes that can be achieved were linked beforehand to the size of the substrate, which comprised two orifices for circulating the fluid in the chamber. The presence of these orifices in the substrate, the surface area of which added to those of the conductivity and temperature sensors, thus constituted a limiting factor for producing small-sized chambers.

The assembling of the elements of the cell also comprises, for example, seals for improving the leak-tightness of the assembly. A low pressure value, obtained by tightening between the two parts of the case, is then sufficient to keep the elements together so as to ensure the leak-tightness. Thus, there is no need to bond the elements together, which makes it possible especially to remove the organic contaminants originating from an adhesive and leading to measurement errors in the case of TOC measurement.

For example, the device comprises a means for measuring the temperature in the measuring chamber. The temperature measuring means is, for example, a thermistor.

According to one embodiment example, the thermistor is housed in a measuring electrode.

According to an embodiment without a substrate, the measuring electrode comprising the thermistor is introduced into the measuring chamber via an orifice formed laterally in the hydraulic body. Thus, the electrode is positioned across the stream of fluid; it crosses the flow, if possible orthogonally so as better to ensure its immersion in the sample.

As regards the sources of contamination, particles originating from the various constituent materials of the cell and in contact with the fluid to be measured are extremely critical for the measurements of very low contents (i.e. from 1 to 10 ppb, for example).

Studies and tests were performed on hydraulic bodies made of various materials and are summarised in the following table:

| Constituent material of the body | Leaching of the base with ultra-pure water | | Manufacturing process |
|---|---|---|---|
| | ppb/min | µS/cm/min | |
| Silicone | 200 | 0.988 | |
| PTFE (Teflon) | 5 | 0.1187 | Injection moulding |
| Anodised alumina | 0.9 | 0.064 | Machining |
| 316 stainless steel | 1.3 | 0.069 | Machining |
| Machinable ceramic (MACOR ®) | <0.3 | <0.058 | Machining |
| Ceramic (with 1% binder removed during the firing process) | 0.6 | 0.061 | Injection moulding |

All the percentages relating to the compositions are given here as mass percentages.

It resulted therefrom that a hydraulic body made of ceramic, and in particular of ceramic based on aluminium oxide, proved to be particularly efficient for notably reducing the contaminant content in the fluid.

Preferably, the hydraulic body is made of ceramic comprising at least 16% alumina.

For example, the hydraulic body is made of ceramic (with 1% of binder removed during the ceramic firing process), made, for example, by injection moulding, green-machining or machining. When subjected to leaching with ultra-pure water, it produced pollution of 0.6 ppb/minute and a conductivity variation of 0.061 µS/cm/minute.

For example, the ceramic of the hydraulic body is a machinable vitroceramic.

According to one example of ceramic obtained by green-machining, the hydraulic body is composed of a ceramic comprising at least 99% alumina, or even 100% alumina, plus or minus a few impurities. Since such a material is obtained, for example, by green-machining, the starting material then comprises a binder (about 1 weight %) consumed during the firing process (after injection into a mould).

Green-machining typically applies to ceramic before firing (unfired state). At this step, the material is still relatively soft (chalky) and may contain certain additives.

According to a particularly advantageous embodiment, a hydraulic body that proved to be particularly efficient is one made of machinable ceramic, having, for example, a composition of the type:

46% silicon dioxide ($SiO_2$)
17% magnesia (MgO)
16% alumina ($Al_2O_3$)
10% potassium oxide ($K_2O$)
7% boron oxide ($B_2O_3$)
4% fluorine (F)

It produced, for its part, pollution of less than 0.3 ppb/minute and a conductivity variation of less than 0.058 µS/cm/min.

An example of a machinable ceramic of this type is MACOR®.

The use of such materials thus allows better resistance to leaching induced by the flows of fluid.

Thus, according to a conceivable embodiment, the hydraulic body is made of injection-moulded ceramic. Or, according to another preferred embodiment, the hydraulic body is made of MACOR®.

Irrespective of the configuration of the cell, it is then particularly advantageous to make the hydraulic body of ceramic containing at least 16% alumina, and preferably of MACOR® so as to minimise the possible sources of contamination.

This is thus a novel aspect per se of the present invention.

Thus, according to another aspect, a device for measuring the conductivity of a liquid is proposed, comprising a UV-transparent window, and a measuring chamber at least partly formed in a separator, the separator being made of ceramic comprising at least 16% alumina, for example of injection-moulded or machinable ceramic, and preferably of MACOR®.

According to one embodiment example, the separator is a hydraulic body as described previously, or a separator as described in document U.S. Pat. No. 6,444,474.

According to another aspect, the chamber may also be made of a noble metal (titanium (Ti), gold (Au) or platinum (Pt), for example). However, for the sake of cost of material, it is industrially difficult to envisage making a hydraulic body of solid noble metal. Metallisation starting with a piece machined from a more standard metal, for instance stainless steel, is, on the other hand, very much more economical. This is a case, for example, of a vacuum metallisation (sputtering) process. Thus, it is possible to machine a piece, for example made of stainless steel, and then to coat its surface with a choice of the following materials, which are given as examples:

noble metals: Pt, Ti, Au;
noble metal oxides: $TiO_2$;
or alloys thereof: $TiO_2$—Pt . . . .

The deposits are produced, for example, by magnetron cathodic sputtering. The piece to be coated is optionally placed in a planetary rotational motion to optimise the coating uniformity.

In addition, prior to deposition, a plasma activation phase may be performed to improve the adhesion of the coating.

This same vacuum metallisation process may also be performed on the various seals in contact with water. The seal then conserves its elasticity and compression properties. A metal fissuring network thus forms at the surface of the seal when it is drawn. Thus, the level of leaching during UV irradiation may be further reduced in the chamber.

Moreover, as mentioned previously, in the case of the application under consideration, the present invention makes it possible to optimise the TOC measuring chamber as regards the volume and thickness of the layer of liquid so that they make it possible to ensure efficient UV photo-oxidation within a reasonable time to avoid measurement drifts due to substantial variations in the temperature of the sample and due to extractions of organic material originating from the materials during the photo-oxidation time.

Independently of the material, another parameter for reducing the oxidation of the materials constituting the cell is to minimise the (S/V) ratio between the surface area (S) of the materials exposed to UV and the volume (V) of the measured sample.

As explained previously, it is preferable to minimise the surface area of exposed materials in order to minimise the leaching. By developing a device as described previously, it is possible to limit the active surface area of the chamber comprising the sensor (consisting, for example, of a substrate, optionally with an FPC, or of individual electrodes—this surface area generally corresponds to the surface area of the bottom of the measuring chamber), preferably free of photo-catalysis electrodes, by placing the fluid inlet and outlet ports parallel to the sensor (and/or to the window), i.e. more generally outside the active surface, of the bottom, and to maximise the sampling volume as a function of the thickness of the fluid (this thickness being limited by the absorption of UV rays as described subsequently with reference to FIG. 13).

Thus, it is possible to miniaturise the cell while at the same time keeping this (S/V) ratio limit less than (or equal to) 2 $mm^2/\mu l$ and while keeping a thickness of readily photo-oxidisable liquid and a reasonable volume and thus being able to measure low TOC values (less than 5 ppb) in a photo-oxidation time of less than 3 minutes.

A device as described previously allows greater latitude of design. Specifically, due to the fact that in the known devices, the substrate was pierced, substrate dimensions existed, and consequently chamber dimensions existed, below which the substrate became too fragile, or even very difficult or impossible to make. Avoiding piercing the substrate thus makes it possible to make cells of much smaller scale.

Thus, according to one embodiment of the invention, the exposed surface area is in total 430 $mm^2$ for a sampling volume of 390 μl. The ratio between the surface area of the material and the sampling volume is thus 1.1 $mm^2/\mu l$, as opposed to at least 13.6 $mm^2/\mu l$ for chambers according to document U.S. Pat. No. 6,444,474. A cell according to one embodiment of the present invention then makes it possible to reduce by a factor of 10 the content of residual particles due to leaching.

The measuring chamber of a device, according to a particularly advantageous embodiment of the invention, thus has a ratio (S/V) of less than or equal to 2 $mm^2/\mu l$, where (S) is the surface area of irradiated material, and (V) is the volume of fluid sample, for example 1.1 $mm^2/\mu l$. Such values were not achievable previously on account of constraints linked to the designs of the prior art devices.

Such ratios are obtained, for example, with a chamber height of less than 4 mm in order for the contained sample as a whole to receive at least 60% of the UV rays, i.e. to conserve enough irradiation power, and to do so while minimising the surface area, which is possible by means of an absence of holes and of photo-catalysis electrodes.

For example, the measuring chamber has a thickness (e) of between 0.5 mm and 4 mm.

According to one embodiment example, the measuring chamber has a volume (V) of greater than or equal to 100 μl, or even preferably greater than or equal to 400 μl.

According to one embodiment example, the measuring chamber has a surface area of irradiated material (S) of less than or equal to 600 $mm^2$.

A low thickness of liquid to be measured maximises the irradiation with UV rays and the positioning of the sensors (mainly the measuring electrodes) does not block out the radiations. This allows rapid and complete oxidation of the organic compounds.

The rinsing and measuring times are reduced and may be readily synchronised with a reference device.

Finally, the conductivity measurement quality correctly temperature-compensated during calibration for different contents of organic particles allows better calibration and greater precision of the associated TOC value subsequently measured.

A device according to the invention thus makes it possible to reduce the leaching residues until a conductivity variation of 0.0055 μS/cm/minute is reached, which means, in other words, down to one thousand times fewer pollutants than in prior art devices under identical conditions.

The present invention is also directed towards a use of a device as described previously, in which the device is positioned such that a flow of liquid in the measuring chamber is vertical and ascending, the inlet channel emerging in the chamber under the outlet channel. The vertical mounting of the cell with the outlet towards the top makes it possible to facilitate the rinsing and degassing.

Finally, the present invention is directed towards a water purification system, comprising a device as described previously, the device being fixed onto an electronic card such that the inlet channel emerges in the chamber under the outlet channel such that a flow of fluid in the measuring chamber is vertical and ascending, the inlet channel and the outlet channel each at least having a portion in the continuation of each other, the portions emerging in the measuring chamber face to face.

Such a system is, for example, a system for producing and purifying water (for instance the commercial product Milli-Q (registered trademark)) or a loop system for distributing purified water.

For example, it also has the following advantages:
it makes it possible to detect low contents of TOC in pure or ultra-pure water, and with better precision,
it has a narrower measuring dispersion,
the measured TOC values are closer to the microelectronic references than other devices,
it has a low design cost (does not require any cavity machining or extrusion),
such a cell is compact,
the rinsing phase is faster.
the oxidation phase is faster.

Figure 2:
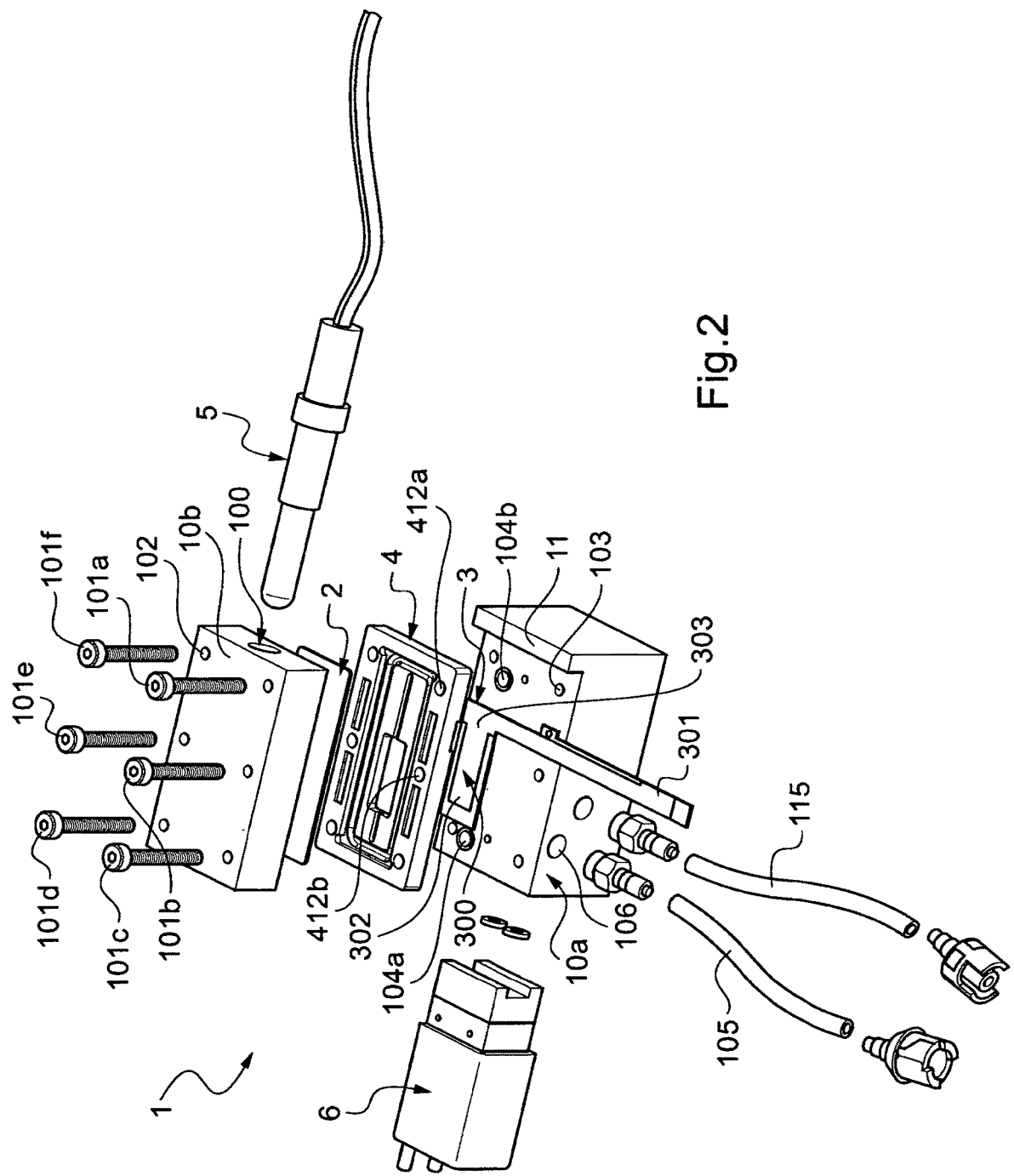
Figure 3:
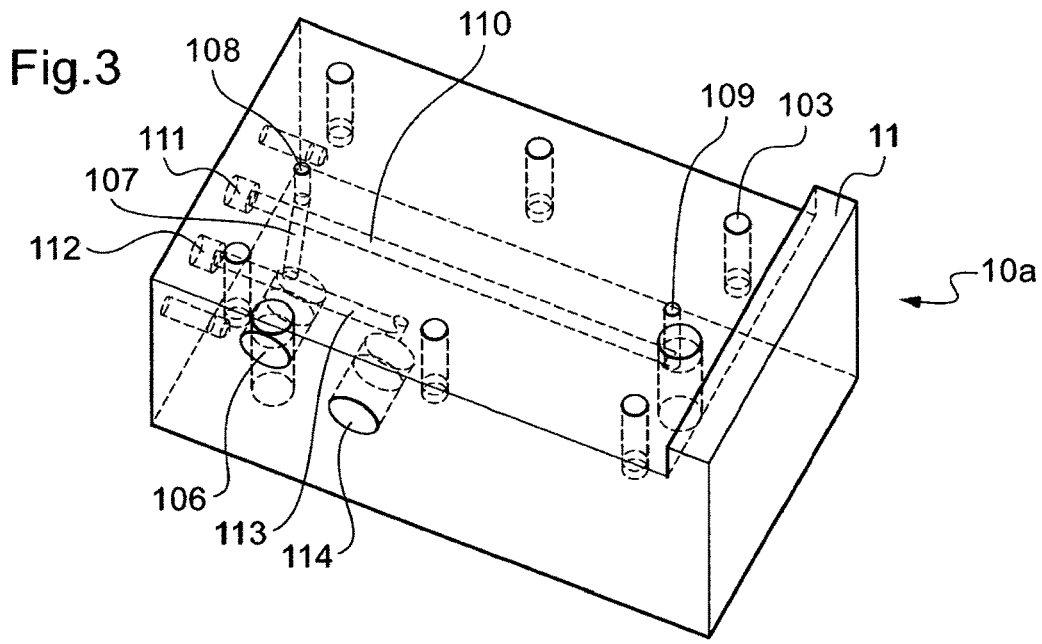
Figure 4:
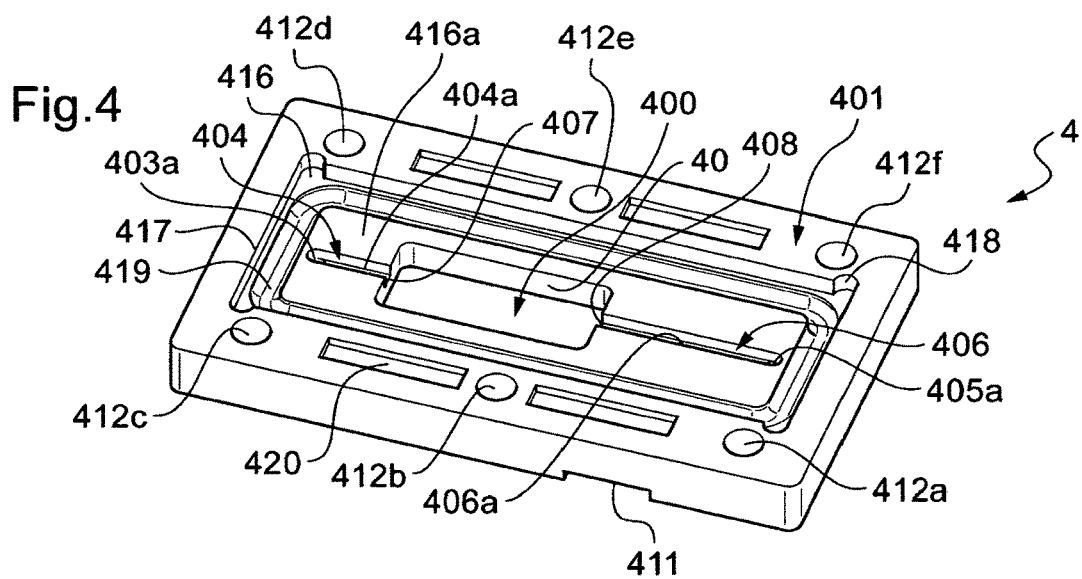
Figure 5:
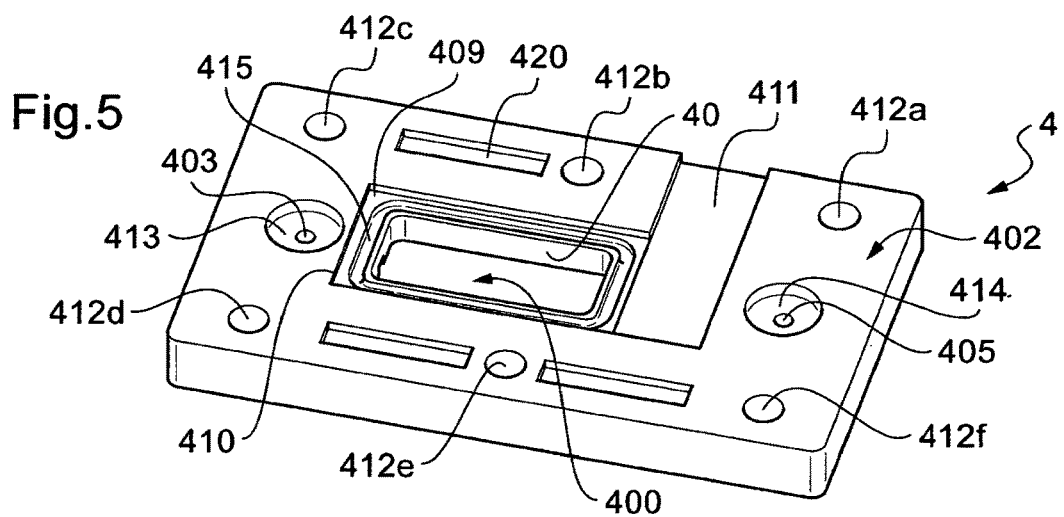
Figure 6:
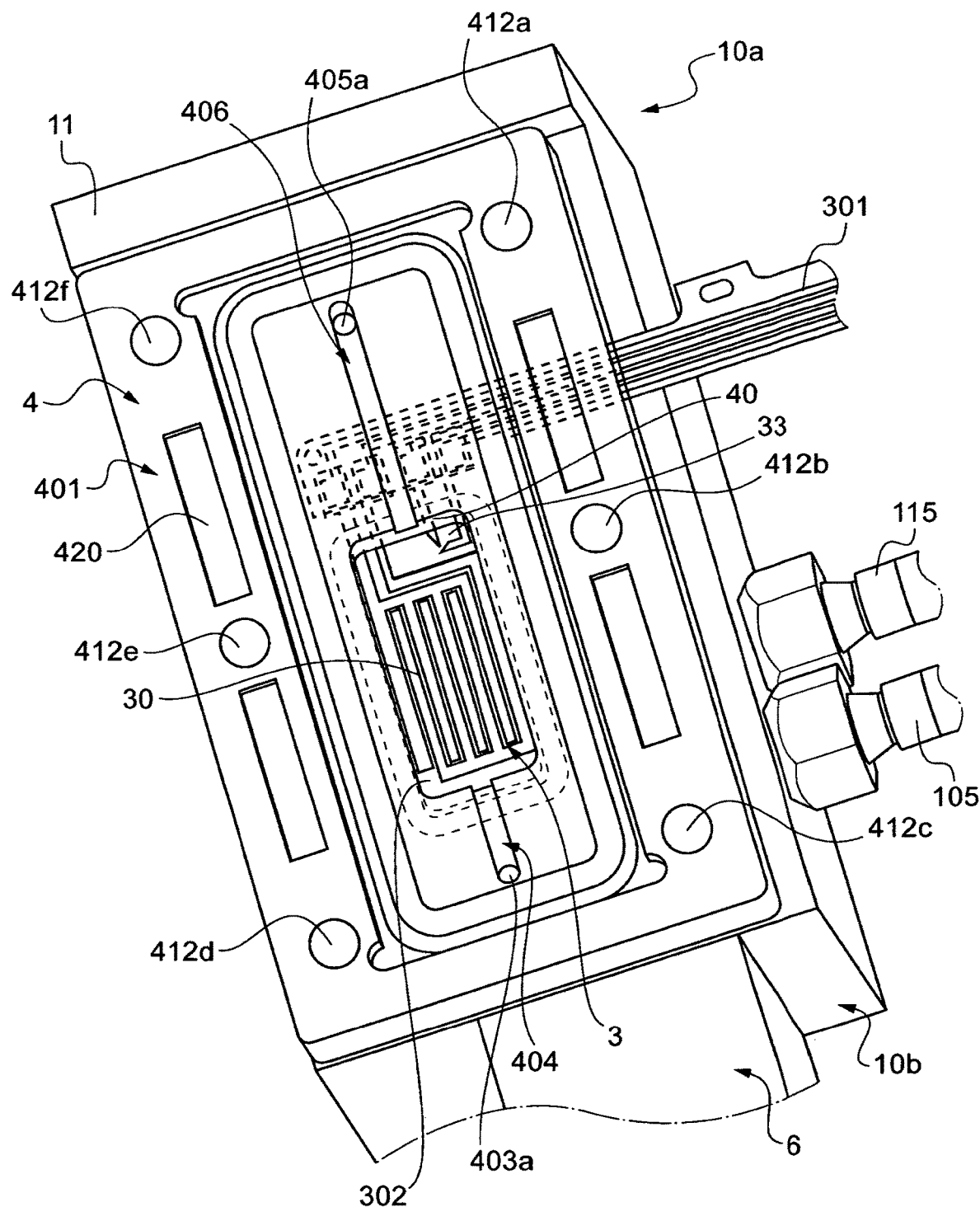
Figure 7:
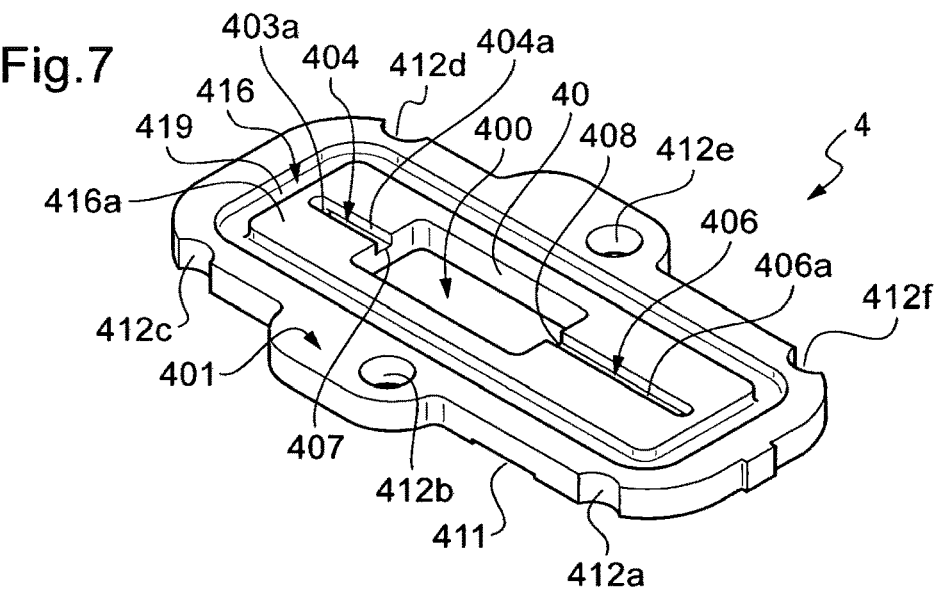
Figure 8:
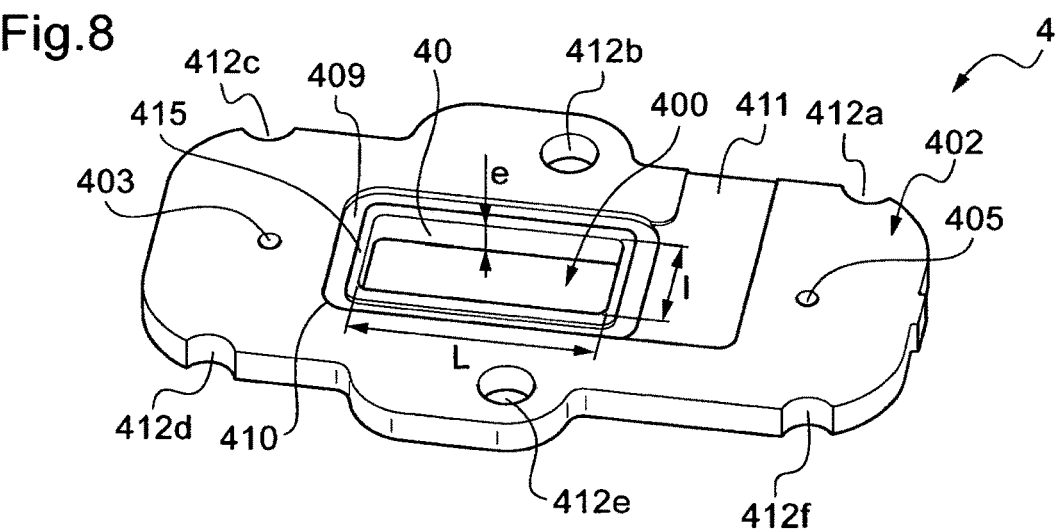
Figure 9:
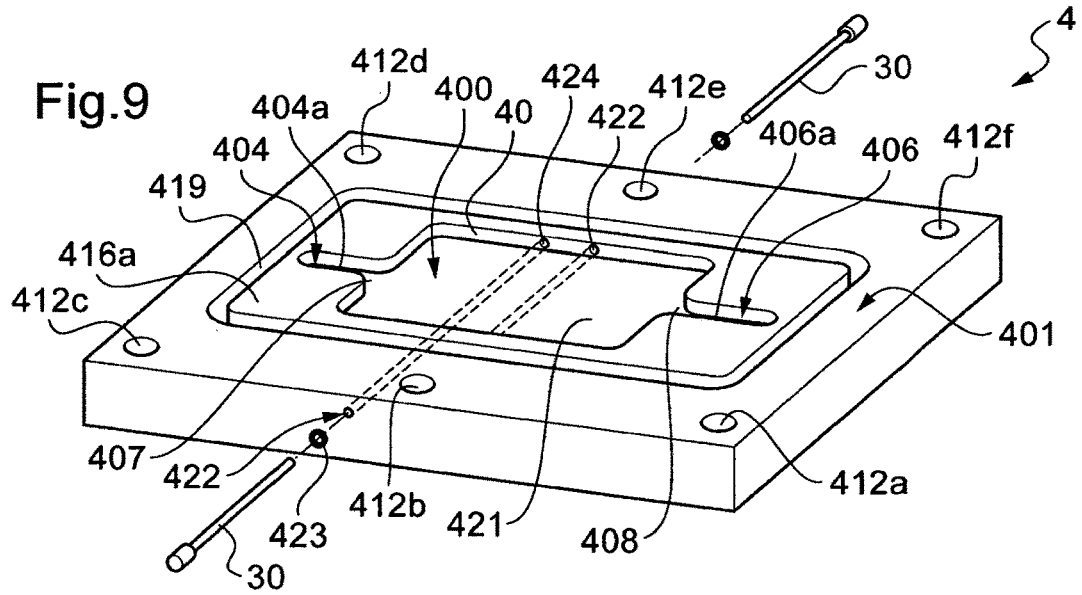
Figure 10:
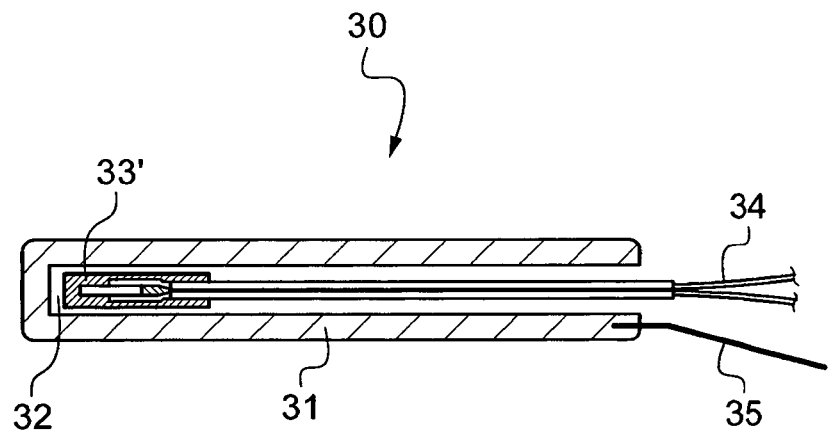
Figure 11:
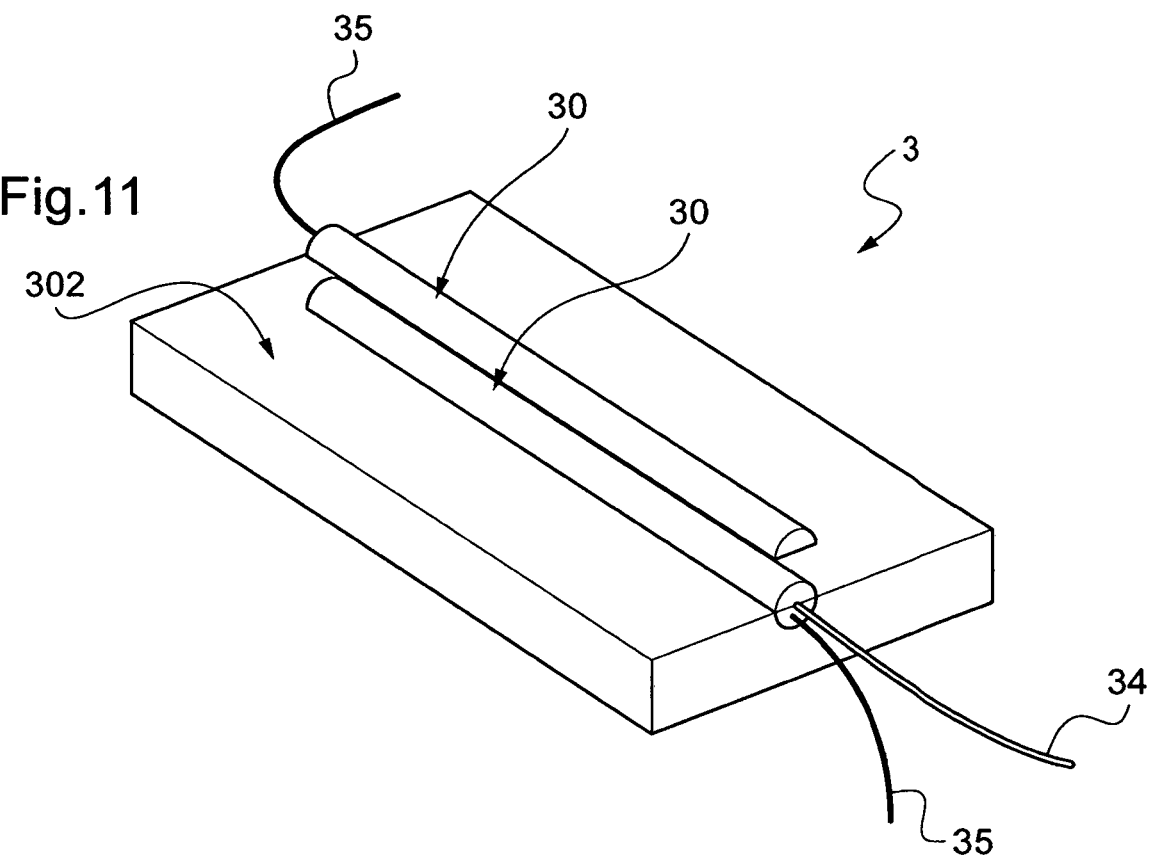

The invention will be clearly understood and the advantages thereof will emerge more clearly on reading the detailed description that follows, with reference to the attached drawings (the scales of which are not representative), which are given as illustrations without any limitation, in which:

FIG. 1 represents various views of a device according to one embodiment of the invention, FIG. 2 is an exploded view of a device according to one embodiment of the invention, FIG. 3 is a view in transparency of a mounting base of a device according to one embodiment example, FIG. 4 shows a hydraulic body viewed from above according to a first embodiment example of the present invention, FIG. 5 illustrates the hydraulic body of FIG. 4 viewed from below, FIG. 6 shows a top view of an assembly of a hydraulic body according to FIGS. 4 and 5, of a substrate comprising printed electrodes and of a mounting base according to one embodiment example, FIG. 7 shows a hydraulic body viewed from above according to a second embodiment example of the present invention, FIG. 8 shows the hydraulic body of FIG. 7 viewed from below, FIG. 9 shows a hydraulic body viewed from above according to a third embodiment example of the present invention, FIG. 10 details an electrode comprising a thermistor which may, for example, be inserted into the hydraulic body of FIG. 9, FIG. 11 is an embodiment example of a substrate overmoulded onto two electrodes as shown in FIG. 10, FIG. 12 is a table collating the sizes and characteristics of measuring chambers described in U.S. Pat. No. 6,444,474 and according to two embodiment examples of the present invention, FIG. 13 demonstrates the absorption of radiation in a layer of water as a function of the depth, FIG. 14 shows curves of extraction as a function of time for assessing the performance of a device according to one embodiment example of the present invention.

It should be pointed out in this regard that the description which follows is that of preferred embodiments, which are given as non-limiting examples.

With reference to FIGS. 1 and 2, a device 1 for measuring the conductivity of an ultra-pure liquid, for example of ultra-pure water, comprises a case 10 made of two parts 10a, 10b. A lower part of the case 10 of the device 1 constitutes a mounting base 10a to which is connected an electrovalve 6, and an upper part of the case 10 mainly constitutes a support 10b for a source of UV rays, in the present case a UV ray lamp 5, by means of a housing 100 (visible in FIG. 2), present in the support 10b, and intended to house therein the lamp 5.

Between the two parts 10a, 10b are housed a UV-transparent window 2 and a hydraulic body 4 comprising a measuring chamber 400 with a base which has here a parallelepiped rectangle overall shape. Thus, the window 2 and the chamber 400 with its base constitute here the conductivity measuring cell. It is described later that the base may be, for example, a substrate 3 or an integral part 421 of the hydraulic body 4, or even an independent plate (not shown).

To take a measurement, the liquid to be analysed is conveyed via a liquid inlet hose 105. This hose is connected on the one hand to a hydraulic circuit of a purification system of the water to be analysed (not shown), and on the other hand to an inlet 106 of the mounting base 10a. As shown in FIG. 3, the mounting base 10a comprises a first pipe 107 connecting the inlet 106 to a first orifice 108, which is positioned facing an inlet 403 of the hydraulic body 4 (visible, for example, in FIG. 5) when the device 1 is assembled.

For the removal of fluid, the mounting base 10a of the device 1 has a second orifice 109 (see FIG. 3), which is positioned facing an outlet 405 of the hydraulic body 4 (see FIG. 5) when the device 1 is assembled. A second pipe 110 connects the second orifice 109 to an electrovalve inlet 111 to which is connected the electrovalve 6 on the one hand. After passing through the electrovalve 6, connected on the other hand to an electrovalve outlet 112 formed in the mounting base 10a, a third pipe 113 connects the electrovalve outlet 112 to an outlet 114 of the device 1. A liquid outlet hose 115 is thus connected on the one hand to a reservoir of measured ultra-pure liquid (not shown), and on the other hand to the outlet 114 of the mounting base 10a.

The liquid thus transits via the inlet hose 105, the first pipe 107 and then an inlet channel 404 of the hydraulic body 4 before arriving in the chamber 400 where the measurement is taken.

Once the measurement has been taken, for example by means of electrodes 30, the liquid is removed via an outlet channel 406 of the hydraulic body 4, it passes via the second pipe 110, via the electrovalve 6 (exiting the mounting base 10a via the electrovalve inlet 111, and re-entering via the electrovalve outlet 112), and then via the third pipe 113, and is finally conveyed to a drain or to the inlet of the water purification system to be recycled, by the outlet hose 115.

The mounting base 10a has, on a side opposite the electrovalve 6, a stop 11 which serves, for example, as a foolproofing for assembling the device 1 and facilitating the positioning of the hydraulic body 4 on the mounting base 10a, especially to ensure that the inlet 403 and the outlet 405 are indeed facing the orifices 108 and 109.

The window 2 is here a simple UV-transparent rectangular plate made, for example, of quartz glass.

According to embodiment examples of FIGS. 1 to 8 and 11 especially, the measuring chamber 400 formed in the hydraulic body 4 has a base formed by a substrate 3, such that the window 2 and the substrate 3 are on either side of a hydraulic body 4.

According to one embodiment example of the substrate, which is shown, for example, in FIGS. 2 and 6, two measuring electrodes 30 are etched onto a part 302 of one face 300 of the substrate 3, referred to hereinbelow as the working zone 302 intended to be in contact with the liquid present in the measuring chamber 400 formed in the hydraulic body 4. In the present embodiment example, the substrate 3 has a rectangular overall shape and is, for example, also made of quartz glass. Besides the electrodes 30, the substrate 3 can support, for example, a temperature sensor 33 or other electronic elements that are necessary and common in this type of device, for instance a microcontroller, which will not be described in further detail herein, as this is familiar to a person skilled in the art. Furthermore, an FPC (flexible printed circuit board) 301 is brazed onto the substrate 3, in the present case onto the face 300 of the substrate 3, and preferably on a part 303 different from the part 302 bearing the electrodes 30. Any necessary electrical contact is then preferably positioned on the part 303 of the base 300 or on the back of the substrate 3 so as to be protected against any contact with the liquid present in the chamber 400. Preferably, the working zone 302 of the face 300 comprises only the electrodes 30, or even optionally the temperature sensor 33, for example a thermistor. In the present embodiment example, the parts 302 and 303 are juxtaposed along a length of the substrate 3, i.e. in a longitudinal direction.

It is more ergonomic for the configuration of the device 1 to be able to have both the liquid inlet hose 105 and outlet hose 115, and the FPC on the same side. And, irrespective of the embodiment of the hydraulic body 4, it is also more practical for the inlet 403 to be positioned towards the electrovalve 6 and for the outlet 405 to be positioned towards the lamp 5 on account of the weights of the electrovalve 6 and the lamp 5, especially when the device 1 is positioned vertically.

In the embodiment example of substrate 3 as shown in FIG. 11, the substrate 3 then mainly consists of a ceramic or silicon plate in which is machined, for example, at least one electrode recess. The substrate 3 comprises here two head-to-tail electrodes 30, at least one of which preferably comprises a thermistor 33', as shown in FIG. 10. Thus, the substrate 3 according to the embodiment of FIG. 11 is formed from the working zone 302.

Such an electrode 30 is composed, for example, of an electrically conductive body 31, which is thermally conductive if the electrode comprises a thermistor (for example made of titanium, optionally coated with platinum or gold) to which is connected a cable 35 for retrieving the measurement, for example for connection to a computer (not shown). Where appropriate, an electrode 30 comprises a thermistor 33' immersed in a heat-conducting binder filling a space 32, and also connected to a measurement retrieval system via a connection cable 34 (for example for connection to a computer, not shown). The electrode may also comprise any other necessary cabling, for example for earthing or the like.

Two electrodes have, for example, one of the following configurations:

| Length of an electrode (mm) | Diameter (mm) | Distance between two electrodes (mm) |
| --- | --- | --- |
| 18 | 1.2 | 1 |
| 18 | 1.2 | 0.5 |
| 28 | 1.2 | 1 |
| 28 | 1.2 | 0.5 |
| 18 | 2 | 1 |
| 18 | 2 | 0.5 |
| 28 | 2 | 0.5 |

The hydraulic body 4 comprises a hydraulic circuit enabling the fluid to be conveyed to the measuring chamber 400, to be analysed and then removed. It has a parallelepiped rectangle overall shape, and is preferably made of ceramic based on at least 16% alumina, and preferably vitroceramic, of injected ceramic, or of machinable ceramic, or, for example, of MACOR®, as explained previously.

The hydraulic body 4 mainly has a first surface 401, against at least a part of which is positioned the window 2, and a second surface 402 comprising the base of the chamber 400. In the embodiment example of FIGS. 2 and 3 to 8, for example, the base of the chamber 400 is formed by the substrate 3, which is then positioned against a part of the second surface 402. According to the present embodiment example, the second surface 402 is opposite and parallel to the first surface 401.

According to this embodiment example, the chamber 400 is formed passing through the hydraulic body 4 such that it emerges on one side on the first surface 401 of the hydraulic body 4 and on another side on the second surface 402 of the hydraulic body 4. It is formed at the core, in the hydraulic body 4, but is, for example, possibly eccentric for the passage of an FPC, as is detailed hereinbelow.

Thus, the device 1 has an arrangement such that the substrate 3 is positioned against a part of the second surface 402 of the hydraulic body 4, between the hydraulic body 4 and the mounting base 10a. It is thus considered here that the second surface 402 is a lower surface of hydraulic body 4. The window 2 is, itself, located between the support 10b of the lamp 5 and the hydraulic body 4, against at least a part of the first surface 401 of the hydraulic body 4. It is thus considered here that the first surface 401 is an upper surface.

Needless to say, the terms "lower", "upper", "first" and "second" are arbitrary and are used herein merely for the sake of clarity with reference to the figures.

More precisely, the window 2 is positioned so as to be both facing the chamber 400 and an aperture 100 (not visible in the figures) for housing the lamp 5 allowing irradiation focused on a liquid sample contained in the chamber 400. Similarly, the substrate 3 is positioned against a part of the second surface 402 such that the electrodes 30 present on the working zone 302 are facing the chamber 400.

Thus, the UV-transparent window 2 covers at least a part of the first surface 401 by closing the chamber 400 on the side of the first surface 401, and the substrate 3 covers a part of the second surface 402 by closing the chamber 400 on the side of the second surface 402.

For the circulation of the fluid, the hydraulic body 4 comprises an inlet 403 for feeding the chamber 400 with liquid to be measured and an outlet 405 for removing the liquid once measured, the inlet 403 and the outlet 405 being located outside the part of the second surface 402 covered by the substrate 3. This makes it possible, inter alia, to avoid any machining or piercing of the substrate 3 for the circulation of the fluid in the device 1. The absence of holes in the working zone 302 of the substrate 3 also makes it possible to reduce the surface of this working zone, which is the surface exposed to the UV rays. This reduction is also facilitated by the absence of photo-oxidation electrodes which are occasionally in addition to the measuring electrodes 30.

In the present embodiment example, the inlet 403 and the outlet 405 are formed in the second surface 402 outside a positioning zone of the substrate 3, or such that it is possible to position the substrate 3 against the second surface 402 with the working zone 302 facing the chamber 4 without the substrate 3 obstructing either the inlet 403 or the outlet 405.

In the hydraulic body 4, an inlet channel 404 is connected to the inlet 403, and an outlet channel 406 is connected to the outlet 405, the inlet channel 404 and the outlet channel 406 both emerging in the chamber 400, respectively at ports 407 and 408 formed in a side wall 40 of the chamber 400, as illustrated in FIGS. 4, 7 and 9. It is noted, for example in FIGS. 4 and 7, that the outlet channel 406 is longer here than the inlet channel 404, this being linked to the eccentricity of the chamber 400 mentioned previously. Specifically, as shown in FIGS. 5 and 8, the second surface 402 has several recesses 409, 411, which, serve especially for positioning the substrate 3 comprising an FPC. A recess 409, delimited by a contour 410 surrounding the chamber 400, makes it possible to position the substrate 3 thereat such that the working zone 302 comprising the electrodes 30 is facing the chamber 400. It is also hollowed into the hydraulic body 4 and, here, has a size adjusted to at least a part of the substrate 3 so as to house therein the substrate 3 in order for the working zone 302 of the face 300 to be positioned as centred as possible relative to the chamber 400. The contour 410 might, however, have any shape as long as it enables positioning of the substrate 3 with its working zone 302 facing the chamber 400. Another recess is formed in a hollow 411 intersecting with the recess 409 to pass the brazed FPC 301 onto the substrate 3. In the present embodiment example, since the FPC 301 is brazed to the substrate 3 via the part 303 of the face 300, and since the working zone 302 of the face 300 comprising the electrodes is facing the chamber 400, it is preferable for the hollow 411 to have a depth greater than the recess 409 intended for the substrate. Via this arrangement of the substrate 3, the outlet channel 406 is longer than the inlet channel 404 so as to connect the chamber 400 to the outlet 405, by straddling the part 303 of the face 300 of the substrate 3. Needless to say, other configurations may be envisaged without departing from the scope of the present invention, for instance reversing this dissymmetry so that the part 303 is located at the inlet 403, for example, or alternatively such that the part 303 is no longer located in a longitudinal continuation of the working zone 302 but is, for example, juxtaposed along a width of the substrate. However, the present configuration has, for example, the advantage of making it possible to pass the FPC 301 outside the device 1, without hampering the assembling or the leak-tightness of the assembly.

Thus, in the present implementation example, the hollow 411 is formed between two traversing holes 412a and 412b of the hydraulic body 4 through which pass, respectively, fixing elements 101a and 101b, for holding together the two parts 10a and 10b of the case 10 of the device 1.

In this example, six fixing elements 101 (a to f), which are, for example, screws, are envisaged, but their number is obviously variable. They each pass through a hole 102 made in the support 10b, one of holes 412 (a to f) of the hydraulic body 4, and fix into holes 103 of the mounting base 10a, for example by screwing. The window 2, the hydraulic body 4 and the substrate 3 are thus slightly compressed between the support 10b and the mounting base 10a to ensure leak-tightness, which is optionally reinforced with various seals.

In the implementation example of FIGS. 7 and 8, the hydraulic body 4 has a shape that can especially minimise the amount of material required to produce it. Only the holes 412b and 412e are complete, the others having been truncated.

To reinforce the leak-tightness, for example, the hydraulic body 4 optionally has a reinforcement 413 around the inlet 403 and a reinforcement 414 around the outlet 405 which are intended, for example, each to receive an O-ring seal 104a, 104b (which are visible, for example, in FIG. 2) as shown in the implementation example of FIG. 5, whereas that of FIG. 8 does not have any.

The recess 409, which is intended to receive at least a part of the substrate 3, also comprises, for example, a groove 415, surrounding the chamber 400, to receive therein a seal (not shown) reinforcing the leak-tightness and especially the isolation of the working zone 302 of the part 303 of the substrate 3, for example.

Similarly, with reference to the embodiment of FIG. 4, the first surface 401 comprises a recess 416, delimited by a contour 417 surrounding the chamber 400, intended to receive the window 2. Here, the recess 416 is hollowed out and has a rectangular overall shape. It optionally comprises close to each of its corners a reinforcement 418 formed by a ledge, which is of rounded shape here, in the contour 417. The reinforcements 418 make it possible, for example, to pass a tool or a finger through in order to dislodge the window 2, for example to clean the device 1. Thus, when the window 2 is positioned in its recess 416, the contour 417 is in discontinuous contact with the window 2. As previously, the recess 416 and its contour 417 may have any shape as long as the window is positioned facing the chamber 400 and enables it to be closed. The first surface 401 also has a groove 419 for receiving a seal (not shown) to reinforce the leak-tightness between the chamber 400 and the window 2 when the device 1 is assembled.

In the implementation example of FIG. 7, the recess 416 is formed by the groove 419.

However, in an embodiment in which the groove 419 and the recess 416 are distinct, it is preferable for the groove 419 to be positioned between a contour 417 of the recess 416 and the chamber 400.

In these implementation examples, the contour 417 of the recess 416, or even the groove 419 if it exists, surrounds not only the chamber 400 but also at least a portion of the inlet channel 404 and of the outlet channel 406 so that a port 403a linked to the inlet 403 via a portion of the inlet channel 404 and a port 405a linked to the outlet 405 via a portion of the outlet channel 406 are within the zone delimited by the groove 419 if it exists or the contour 417, i.e. that of the two which is the closer to the chamber 400.

The ports 403a and 405a are not necessarily located in line with the inlet 403 and the outlet 405. They may be offset, for example recentred, close to each other relative to the inlet 403 and the outlet 405. This means that, per se, the inlet 403 and the outlet 405 may be located outside the contour 417 and/or the groove 419 if it were plotted identically on the second surface 402 of the hydraulic body 4.

The inlet channel 404 and the outlet channel 406 then have, for example, an obtuse angle, i.e. greater than a right angle as illustrated in the present implementation example. An obtuse angle is also preferable to an acute angle to avoid disrupting the flow.

In order to promote the flow by minimising the formation of bubbles or turbulence, it is preferable for the inlet channel 404 and the outlet channel 406 to emerge in the chamber 400 parallel to the base of the chamber 400, in this case the substrate 3, and/or of the window 2. The inlet channel 404 has a portion 404a between the port 403a and the port 407 parallel to the base of the chamber 400, and which is also in this case rectilinear, and the outlet channel 406 has a portion 406a between the port 405a and the port 408 parallel to the base of the chamber 400, and also in this case rectilinear. Furthermore, the portions 404a and 406a are in the present case in the continuation of each other and facing each other.

To facilitate the production and/or maintenance of the hydraulic body, the portions 404a and 406a are open, i.e. formed by grooves hollowed into the first surface 401, in the recess 416, such that the flow is directed and the channels 404 and 406 are closed up to the ports 407 and 408 by the window 2, tangential, and in leak-tight contact with at least a part 416a directly surrounding the chamber 400 and the portions 404a and 406a of the channels 404 and 406. Such a design of the inlet channel 404 and outlet channel 406 thus allows easy cleaning of all of the hydraulic circuit of the hydraulic body 4 since all the parts of the circuit are visible, and accessible. Furthermore, a bend formed in the inlet channel 404 and outlet channel 406 is preferably rounded to limit any formation of turbulence in the flow.

Finally, the hydraulic body 4 optionally comprises other different recesses, for example hollowed-out rectangular recesses 420 (for example in the embodiment of FIGS. 4 and 5), making it possible, for example, to add various leak-tightness seals if necessary, in order to be able to engage with complementary forms of the case 10 for the production of the assembly of the device 1.

Various forms of seals may be made, for instance seals with a lip to follow the shape of the hydraulic body and to prevent a dead volume of water in the part 416a.

The materials of the seals are selected so as to have little organic residue expelled during irradiation with UV rays and on contact with pure or ultra-pure water. These materials may be based on fluorocarbon polymer, for example (PTFE, PEEK, Viton®, nitrile, etc.). These seals may be obtained conventionally by moulding or pressing, for example.

The embodiment of FIG. 9 shows a hydraulic body 4 in which the chamber 400 comprises a base 421 forming here an integral part of the hydraulic body 4. It may also be an independent plate, optionally made of the same material, for example.

The chamber 400 is, in the present case, centred along the width and the length relative to the hydraulic body 4 due to the absence of FPC on a substrate, but its depth is less than that of the hydraulic body 4 such that base 421 is tangential to the portions 404a and 406a of the inlet channel 404 and the outlet channel 406. Thus, the portions 404a and 406a are both tangential to the base 421 and to the part 416a, and have a height identical to the thickness of the chamber 400.

Furthermore, the ports 407 and 408 have a flared funnel shape, so as to further minimise the flow disruptions.

The sensors are made in the present case by two head-to-tail electrodes 30, at least one of which preferably comprises a thermistor, inserted on either side of the hydraulic body 4 via channels 422 (optionally provided with a seal 423). The electrodes 30 are, for example, of the type described previously with reference to FIG. 10. Optionally, a reinforcement 424 makes it possible to receive one end of the electrode 30 in order to prevent it from being out of plumb in its channel 422. Furthermore, the electrodes 30 are, for example, positioned transversely relative to the flow, or even orthogonally. This makes it possible to better ensure their total immersion irrespective of the orientation of the measuring chamber 400 (which is occasionally positioned vertically).

The various characteristics presented with reference to the three embodiments detailed previously may, of course, be combined according to need with the evaluation of a person skilled in the art.

FIG. 12 presents various embodiments of the dimensions of the chamber 400, and makes it possible to compare the corresponding ratios (S/V) with those of the devices presented in document U.S. Pat. No. 6,444,474.

The chamber 400, of parallelepiped rectangle overall shape, has, for example with reference to the first line relating to the present invention, a length (L) of 18.4 mm, a width (l) of 8 mm and a thickness (e) of 2.7 mm, i.e. a volume (V) of about 397 µl. The total irradiated surface area (S) is determined by the following formula: 2*surface area exposed to the rays (s=L*l)+side surface (2*(L+l)*e).

In the present case, the total irradiated surface area is:

$$2*(18.4*8)+2*(18.4+8)*2.7=436.96 \text{ mm}^2.$$

Thus, the dimensions of the elements are such that the ratio (S/V) is 436.96/397=1.1 mm$^2$/µl.

This table thus shows, for various chamber dimensions, the influence of the thickness and the active surface area on the ratio (S/V). A thickness of less than 150 µm and a water volume of less than 30 µl coupled with photo-catalysis electrodes, as indicated in U.S. Pat. No. 6,444,474, allow very rapid photo-oxidation of the fluid but give a ratio (S/V) of greater than 13 mm$^2$/µl irrespective of the chamber geometry, the extractables generator then preventing measurements of low TOC. The inlet and outlet for the fluid in the measuring chamber parallel to the UV radiation and the photo-catalysis electrodes require space, preventing miniaturisation of the chamber, or even of the cell.

Since the present invention makes it possible especially to minimise the surface area (S) of irradiated materials while at the same time maximising the volume (V), it is thus possible to reduce the ratios (S/V).

However, the volume (V) is limited by the thickness (e) of the chamber 400.

Figure 13:
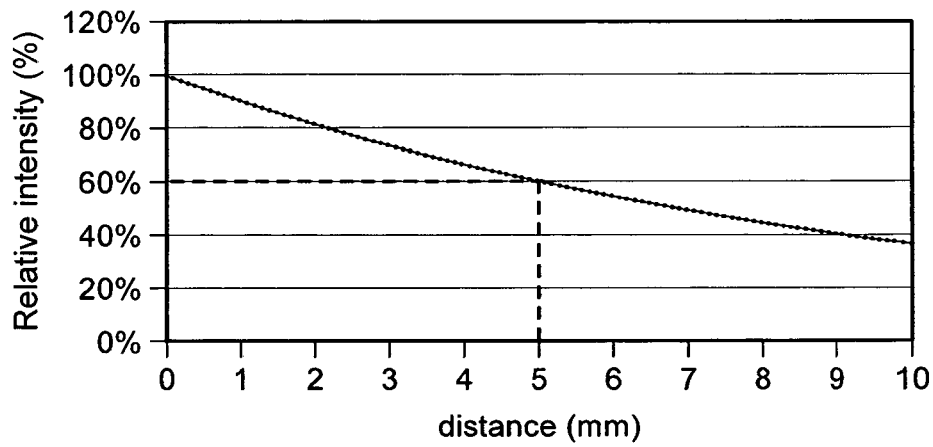
Figure 14:
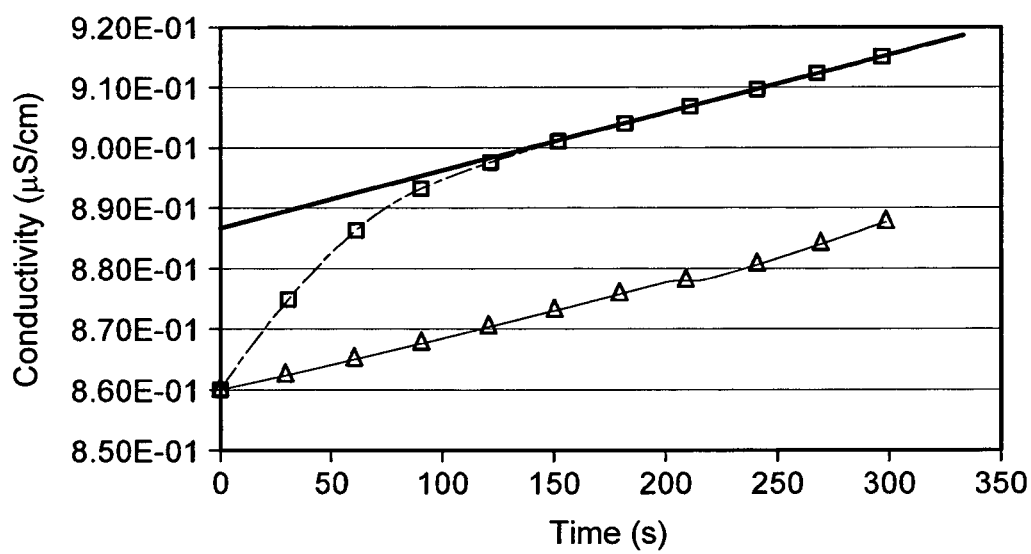

Specifically, as shown in FIG. 13, the relative intensity of the UV rays decreases greatly as a function of the depth in the fluid (in the present case ultra-pure water). Thus, beyond a certain thickness of the sample, and thus of the chamber 400, the radiation weakens such that the irradiation of the sample is less efficient. Consequently, it is preferable for the thickness of the chamber to remain less than or equal to 5 mm in order for all of the sample of fluid to be at least 60% irradiated by the applied UV rays.

FIG. 14, to be compared with the "triangle" curve of FIG. 5 of document U.S. Pat. No. 6,444,474, thus makes it possible to assess the advantages in terms of leaching afforded by the present invention in the case where the device is made of MACOR®. FIG. 14 shows the change in conductivity (in µS/cm) as a function of the time (in seconds). The curve with the "squares" shows the change in conductivity of a pure water initially comprising 10 ppb of organic compounds, and the curve with the "triangles" shows the change in conductivity in deionised water (serving as a control for assessing the leaching of the device).

Theoretically, the conductivity after oxidation of a pure water, initially at 0.86 µS/cm comprising 10 ppb of organic compounds, reaches 0.8995 µS/cm, i.e. an increase of 4%.

As shown by the "triangle" curve of FIG. 5 of document U.S. Pat. No. 6,444,474, the leaching produces a conductivity variation of 5.2 µS/cm/min, which would induce a constant error of 520%. A 2.6% variation is thus not detectable.

As shown by FIG. 14, a device according to the invention makes it possible to measure contents that are a thousand times smaller. The leaching according to the "triangle" curve shows a change in conductivity due to leaching of 0.0055 µS/cm/min, which thus makes it possible to perform analyses at a level of a few ppb.

Needless to say, the present invention is not limited to the preceding description, but covers any variant in the context of the claims hereinbelow.

The invention claimed is:

1. Device for measuring the conductivity of a liquid, comprising a ceramic hydraulic body having a measuring chamber formed therein for containing a sampling volume to be irradiated with ultraviolet (UV) rays, said measuring chamber being defined in said ceramic hydraulic body by a base of said ceramic hydraulic body and by side walls of said ceramic hydraulic body extending from said base, a UV-transparent window being located between the measuring chamber and a source of UV rays, hermetically closing a first side of the measuring chamber, the measuring chamber opening at least on the first side onto a first surface of said ceramic hydraulic body and being closed on one side of a second surface of said ceramic hydraulic body by said base, the UV-transparent window covering at least part of the first surface, closing the measuring chamber hermetically on the side of the first surface, and wherein an inlet channel is formed in said ceramic hydraulic body for feeding the measuring chamber with liquid to be measured and an outlet channel is formed in said ceramic hydraulic body for removing the measured liquid from the measuring chamber, the inlet channel and the outlet channel emerging on either side beyond a surface exposed to UV rays, and only the sampling volume contained in the measuring chamber is irradiated, wherein said base comprises two electrodes positioned in said measuring chamber, and wherein the measuring chamber has a thickness of between 0.5 mm and 4 mm, a volume of greater than or equal to 400 µl and a surface area of irradiated material of less than or equal to 600 mm$^2$.

2. Device according to claim 1, wherein said ceramic hydraulic body comprises an inlet to which is connected the inlet channel, and an outlet to which is connected the outlet channel, the inlet channel having an inlet channel port emerging in the measuring chamber via one of said side walls laterally delimiting the measuring chamber, and said outlet channel having an outlet channel port emerging in the chamber via another one of said side walls laterally delimiting the measuring chamber.

3. Device according to claim 1, wherein the second surface of said ceramic hydraulic body comprises a recess delimited by a contour surrounding the measuring chamber to position the base comprising electrodes such that the electrodes are facing the measuring chamber, and the recess being hollowed into said ceramic hydraulic body and having a size adjusted to the base to house it therein.

4. Device according to claim 1, wherein the first surface of said ceramic hydraulic body comprises a recess delimited by a contour surrounding the measuring chamber, to position the UV-transparent window, and the recess being hollowed into said ceramic hydraulic body and having a size adjusted to the window to house it therein.

5. Device according to claim 1, wherein said ceramic hydraulic body is made of ceramic comprising at least 16 weight % of alumina.

6. Device according to claim 5, wherein the ceramic of said ceramic hydraulic body is a machinable vitroceramic.

7. Device according to claim 5, wherein said ceramic hydraulic body is composed of a ceramic comprising at least 99% alumina.

8. A method of using a device according to claim 1, comprising positioning such that a flow of fluid in the measuring chamber is vertical and ascending, the inlet channel having an inlet port emerging in the measuring chamber under the outlet channel.

9. Water purification system, comprising a device according to claim 1, the device being fixed onto an electronic card such that an inlet port of the inlet channel emerges in the measuring chamber under the outlet channel such that a flow of fluid in the measuring chamber is vertical and ascending, the inlet channel and the outlet channel each having at least a portion in the continuation of each other, the portions emerging in the measuring chamber face to face.

10. The device according to claim 1, wherein one of said two electrode is a measuring electrode, and wherein said device further comprises a thermistor housed in said measuring electrode, wherein said measuring electrode comprising the thermistor is introduced into said measuring chamber via an orifice formed laterally in said ceramic hydraulic body.

* * * * *